US008374892B2

(12) United States Patent
Chang et al.

(10) Patent No.: US 8,374,892 B2
(45) Date of Patent: Feb. 12, 2013

(54) METHOD FOR RETRIEVING A TUMOR CONTOUR OF AN IMAGE PROCESSING SYSTEM

(75) Inventors: King Jen Chang, Taipei (TW); Wen Hwa Chen, Taipei (TW); Argon Chen, Zhonghe (TW); Chiung Nein Chen, Jiali Township, Tainan County (TW); Ming Chih Ho, Taipei (TW); Hao Chih Tai, Taipei (TW); Ming Hsun Wu, Taipei (TW); Po Wei Tsai, Yonghe (TW)

(73) Assignee: AmCad BioMed Corporation, Taipei (TW)

( * ) Notice: Subject to any disclaimer, the term of this patent is extended or adjusted under 35 U.S.C. 154(b) by 399 days.

(21) Appl. No.: 12/693,205

(22) Filed: Jan. 25, 2010

(65) Prior Publication Data

US 2011/0182489 A1 Jul. 28, 2011

(51) Int. Cl.
*G06Q 10/00* (2012.01)
*G06K 9/00* (2006.01)
(52) U.S. Cl. .......................................... 705/3; 382/128
(58) Field of Classification Search ............... 382/128; 705/2–3
See application file for complete search history.

(56) References Cited

U.S. PATENT DOCUMENTS 7,848,592 B2 * 12/2010 Chen et al. ..................... 382/283

* cited by examiner

*Primary Examiner* — Hiep V Nguyen
(74) *Attorney, Agent, or Firm* — Muncy, Geissler, Olds & Lowe, PLLC

(57) ABSTRACT

The present invention related to a method for retrieving a tumor contour of an image processing system that includes a memory storing a grayscale image and a processor, comprising: receiving an input tumor contour of the grayscale image; defining a tumor contour annular region and a plurality of reference segments of the grayscale image, wherein the input tumor contour is in the tumor contour annular region, and each of the plurality of reference segments is across the tumor contour annular region and includes a plurality of measured points; retrieving a tumor contour suggestion point on each of the plurality of reference segments; and linking all the tumor contour suggestion points on all of the reference segments, for forming the tumor contour. Accordingly, by applying the method of the present invention, a doctor can rapidly and accurately identify the contour of a tumor in a grayscale image.

6 Claims, 11 Drawing Sheets calculating a gradient variance of the grayscale image in the plurality of local segments and an average gradient variance of the grayscale image in the plurality of moving horizons calculating the ratio of the gradient variance of the grayscale image in the plurality of local segments to the average gradient variance of the grayscale image in the plurality of moving horizons retrieving the measured point corresponding to the maximum ratio as the tumor contour suggestion point

FIG. 5 calculating gradients of the grayscale image in the plurality of reference segments and an average gradient of the grayscale image in the plurality of contrast reference segments calculating the differences between the gradients of the grayscale image in the plurality of reference segments and an average gradient of the grayscale image in the plurality of contrast reference segments retrieving the measured point corresponding to the maximum difference as the tumor contour suggestion point

FIG. 9 when there are no tumor contour suggestion points before, taking one of the plurality of measured points on the first reference segment as a first point, or when there is one tumor contour suggestion point before, taking a last tumor contour suggestion point on one of the plurality of reference segments as the first point; taking one of the plurality of measured points on the next reference segment as a second point retrieving the measured point on the next reference segment, having the minimum distance between the first point and the second point as the tumor contour suggestion point on the next reference point

FIG. 10 when there are no tumor contour suggestion points before, taking one of plurality of measured points on the first reference segment as a reference list; or when there is one tumor contour suggestion point before, taking all of the pervious tumor contour suggestion points as the reference list providing an EWMA weighting formula determining the weighting factor of the EWMA weighting formula and receiving the EWMA value of the reference list by the gradients of grayscale image of each of the measured points or the tumor contour suggestion points in the reference list using the EWMA value of the reference list and the gradients of grayscale image of each of the plurality of measured points on the next reference segment as the input variables of the EWMA weighting formula defining the output of the EWMA weighting formula as the EWMA value of each of the plurality of measured points on the next reference segment taking the one of plurality of measured points on the next reference segment, having the minimum difference between the gradient of grayscale image thereof and the EWMA value thereof, as the tumor contour suggestion point on the next reference segment

FIG. 11

```
┌─────────────────────────────────────────────────────────┐
│ when there are no tumor contour suggestion point before │
│ a last tumor contour suggestion point, defining one of  │
│ the plurality of measured points on the first reference │
│ segment as a first point, and one of the plurality of   │
│ measured points on the second reference segment as a    │
│ second point; or when there is one tumor contour        │
│ suggestion point before the last tumor contour          │
│ suggestion point, defining the tumor contour suggestion │
│ point before the last tumor contour suggestion point as │
│ the first point, and defining the last tumor contour    │
│ suggestion point as the second point                    │
└─────────────────────────────────────────────────────────┘
                            │
┌─────────────────────────────────────────────────────────┐
│ defining a vector going from the first point to the second │
│ point as a first vector, and vectors going from the second │
│ point to each of the plurality of measured points on a  │
│ next reference segment as a plurality of second vectors │
└─────────────────────────────────────────────────────────┘
                            │
┌─────────────────────────────────────────────────────────┐
│ calculating the cosine values of the angles included by │
│ the first vector and the plurality of second vectors,   │
│ respectively                                            │
└─────────────────────────────────────────────────────────┘
                            │
┌─────────────────────────────────────────────────────────┐
│ taking the one of plurality of measured points on the   │
│ second next reference segment, being the end point of   │
│ the second vector corresponding to the angle having     │
│ maximum cosine value, as the tumor contour suggestion   │
│ point on the second next reference segment              │
└─────────────────────────────────────────────────────────┘
```

FIG. 12

METHOD FOR RETRIEVING A TUMOR CONTOUR OF AN IMAGE PROCESSING SYSTEM

BACKGROUND OF THE INVENTION

1. Field of the Invention

The present invention relates to a method for retrieving a tumor contour of an image processing system and, more particularly, to a method for retrieving a tumor contour of an image processing system that includes a memory storing a grayscale image and a processor.

2. Description of Related Art

Owing to the non-invasive image-information technique, ultrasonography becomes one of the most acceptable medical tools without serious side effect, and an important radiography for retrieving information from patients applied in clinical diagnosis and medical application. Moreover, since advanced ultrasonography can provide real-time medical imaging with high resolution, it is widely applied in medical examination and diagnosis of tumoral changes.

For example, by way of analyzing the ultrasonographic image in detail, the properties of the tumor can be easily identified by doctors. Thus, ultrasonography can advantageously reduce frequency of tumoral biopsy. In ultrasonography, an imaging contour of a tumor is a principal index for the diagnosis of benignancy and malignancy. If the imaging contour of a tumor obtained from ultrasonography can approximate the real appearance of the tumor, it is beneficial to promote the accuracy of the examination of tumors at the initial stage. In clinical researches, professional doctors often provide the diagnosis of a tumor through description or checklist after the ultrasonographic images are output and checked. However, referring to the same image of the tumor, diagnostic variation between different diagnoses of different doctors still occur.

Therefore, as the technique of computer-aided diagnosis and reading-out of tumor image develops, the identification of tumors assisted by a computer is gradually accomplished in clinical application. Basically, the prerequisite of the examination or identification of tumors is to determine the site of an imaged tumor, i.e. to determine the contour of the imaged tumor. Conventionally, the researchers delineate an imaged tumor to determine the contour of the tumor. However, the definition of the image, the recognition of the researchers for the boundary of the tumor, and the operational condition of the researchers all incur the variation of the determination of the contour of the tumor, and then undesirably affect the examination or identification of the tumor.

One of the advantages for diagnosing the contour of a tumor aided by a computer is that most of the people who know the location of the imaged tumor can depict similar or even the same contour of the tumor. In other words, people are not required to carefully delineate a tumor but only approximately depict the boundary of the tumor with naked eyes. Then, the computer can provide the real boundary of the tumor by algorithm. Hence, the computer-aided diagnosis is invariably highlighted in the research of medical image processing. For example, in 1987, Michael Kass et al. set forth Snake algorithm, in which an initial boundary was determined first and then an optimal boundary was found out sequentially by algorithm. Therefore, Snake algorithm now becomes one of the well-known methods in medical image processing.

Snake algorithm, also called "active contour method", currently becomes the most widely used algorithm in the research of medical image processing. In Snake algorithm, the principal step is to find out delineation of a region with the minimal constraint of the outside region to the delineated region and the minimal influence of the inside image to the delineated region. Owing to the minimal constraint and influence, the delineated region appears as movement of a snake, and performs expansion and contraction.

Snake algorithm can automatically search data in neighboring regions, locally consider data in each region, and retrieve data according to a feature by surrounding a region based on spatial consecution. The advantage illustrated above is the reason why Snake algorithm is called an "active contour method". Snake algorithm is suitable to retrieve data from a line segment, a boundary, and a contour, to dynamically track, and to three-dimensionally comparison. As long as the initially delineated region is near to the contour of the interesting image, Snake algorithm can propose a final contour by recursive calculation. As shown in FIG. 1, the contour of the airplane is retrieved by the conventional Snake algorithm.

When Snake algorithm is applied in an image having a clear boundary, especially in an image having high contrast difference between outside and inside neighborhoods of the boundary, an acceptable result can be obtained. However, the tumor image often has an indistinct boundary or hypoechoicity, or even has no hypoechoicity such that the applied Snake algorithm needs to be modified to depict the contour clearly. Generally, Snake algorithm is applied to investigate the consecution, curvature, and local gradient energy of each point in the regions (n×n mask) surrounding an predetermined point. However, if the regions surrounding the predetermined point are indistinct, the search result of the regions surrounding the predetermined point is poor in Snake algorithm. If most regions surrounding the main predetermined points are indistinct, Snake algorithm cannot propose acceptable results. On the other hand, if calculating regions surrounding the predetermined point is expanded, Snake algorithm consumes long calculating time and still provides unsatisfactory results for large-scaled indistinct images. Furthermore, the calculation of Snake algorithm requires a depicted contour of an initial region given by the researchers. Once the initial region is improperly determined and the image is indistinct, Snake algorithm cannot output an outstanding result in the ultrasonographic imaging of a tumor.

In conclusion, the conventional delineation of a tumor needs to be carefully made by hands of medical professionals. By contrast, Snake algorithm requires an initial approximate contour of a clear predetermined region instead of delineation by hand, and then a subsequent calculation performs the approaching of the real contour in Snake algorithm. Nevertheless, if the input initial contour depicted by hand is required to very close to the actual contour of the predetermined region, it is time-consuming delineation is inevitable. On the other hand, if the input initial contour is quite different from the contour of the predetermined region, the calculation of the approaching is time-consuming since Snake algorithm falls into no boundary calculation at the same time. Hence, Snake algorithm is not suitable to be applied in an image which is not clear.

SUMMARY OF THE INVENTION

The present invention provides a method for retrieving a tumor contour of an image processing system that includes a memory storing a grayscale image and a processor.

The method for retrieving a tumor contour for an image processing system that includes a memory storing a grayscale image and a processor according to the first embodiment of the present invention comprises: receiving an input tumor contour of the grayscale image; defining a tumor contour annular region and a plurality of reference segments of the grayscale image, wherein the input tumor contour is in the tumor contour annular region, and each of the plurality of reference segments is across the tumor contour annular region and includes a plurality of measured points; retrieving a tumor contour suggestion point on each of the plurality of reference segments; and linking all the tumor contour suggestion points on all of the reference segments, for forming the tumor contour.

The method for retrieving a tumor contour for an image processing system that includes a memory storing a grayscale image and a processor according to the second embodiment of the present invention comprises: receiving an input tumor contour of the grayscale image; defining a tumor contour annular region and a plurality of reference segments of the grayscale image, wherein the input tumor contour is in the tumor contour annular region, and each of the plurality of reference segments is across the tumor contour annular region and includes a plurality of measured points; retrieving a modulated tumor contour suggestion point on each of the plurality of reference segments; and linking all the modulated tumor contour suggestion points on all of the reference segments, for forming the modulated tumor contour;

wherein the modulated tumor contour suggestion point on each of the plurality of reference segments is obtained by the following steps: normalizing the value of all the measured points on the reference segment retrieved by a moving variance retrieving method, the value of all the measured points on the reference segment retrieved by a contrast retrieving method, the value of all the measured points on the reference segment retrieved by a distance retrieving method, the value of all the measured points on the reference segment retrieved by a gradient EWMA difference retrieving method, and the value of all the measured points on the reference segment retrieved by an angle retrieving method into value between 0 and 1; determining modulating criteria for each of the aforementioned retrieving methods; calculating a weighting parameter for each the measured points on the reference segment, by multiplying product corresponding to each of the aforementioned retrieving methods together, wherein each of the products is obtained by multiple the normalized value of the measured point for the number of times equal to the modulating criteria of the corresponding retrieving method, respectively; and retrieving the coordinate of the tumor contour suggestion point on the reference segment by calculating the average coordinate, from the sum of the product obtained by multiplying the coordinate of each of the measured points on the reference segment with the corresponding weighting parameter, respectively;

wherein in the moving variance retrieving method, each of the plurality of reference segments includes a plurality of local segments and each of the plurality of local segments includes a plurality of moving horizons; each of the plurality of local segments consists of one of the plurality of measured points, at least one measured point before and at least one measured point after the one of the plurality of measured points, and each of the plurality of moving horizons consists of one of the plurality of measured points in the corresponding local segment and at least one measured point after the one of the plurality of measured points; and the value of all the measured points on the reference segment are retrieved by the moving variance retrieving method comprising the steps of: calculating a gradient variance of the grayscale image in the plurality of local segments and an average gradient variance of the grayscale image in the plurality of moving horizons; calculating the ratio of the gradient variance of the grayscale image in the plurality of local segments to the average gradient variance of the grayscale image in the plurality of moving horizons; and retrieving the measured point corresponding to the maximum ratio as the tumor contour suggestion point;

wherein in the contrast retrieving method, a center of gravity of the input tumor contour is retrieved and a plurality of contrast reference segments is defined, each of the plurality of contrast reference segments extends from the center of the gravity to of the corresponding reference segments, respectively; and the value of all the measured points on the reference segment are retrieved by the contrast retrieving method comprising the steps of: calculating gradients of the grayscale image in the plurality of reference segments and an average gradient of the grayscale image in the plurality of contrast reference segments; calculating the differences between the gradients of the grayscale image in the plurality of reference segments and an average gradient of the grayscale image in the plurality of contrast reference segments; and retrieving the measured point corresponding to the maximum difference as the tumor contour suggestion point;

wherein in the distance retrieving method, the value of all the measured points on the reference segment are retrieved in sequence by the distance retrieving method comprising the steps of: when there are no tumor contour suggestion points before, taking one of the plurality of measured points on the first reference segment as a first point, or when there is one tumor contour suggestion point before, taking a last tumor contour suggestion point on one of the plurality of reference segments as the first point; taking one of the plurality of measured points on the next reference segment as a second point; and retrieving the measured point on the next reference segment, having the minimum distance between the first point and the second point as the tumor contour suggestion point on the next reference point;

wherein in the gradient EWMA difference retrieving method, the value of all the measured points on the reference segment are retrieved in sequence by the gradient EWMA difference retrieving method comprising the steps of: when there are no tumor contour suggestion points before, taking one of plurality of measured points on the first reference segment as a reference list; or when there is one tumor contour suggestion point before, taking all of the pervious tumor contour suggestion points as the reference list; providing an EWMA weighting formula; determining the weighting factor of the EWMA weighting formula and receiving the EWMA value of the reference list by the gradients of grayscale image of each of the measured points or the tumor contour suggestion points in the reference list; using the EWMA value of the reference list and the gradients of grayscale image of each of the plurality of measured points on the next reference segment as the input variables of the EWMA weighting formula; defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment;

wherein in the angle retrieving method, the value of all the measured points on the reference segment are retrieved in sequence by the angle retrieving method comprising the steps of: when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point; defining a vector going from the first point to the second point as a first vector, and vectors going from the second point to each of the plurality of measured points on a next reference segment as a plurality of second vectors; calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

Accordingly, by applying the method for retrieving a tumor contour of an image processing system of the present invention, a doctor can rapidly and accurately identify the contour of a tumor in a grayscale image. Besides, since the tumor contour can be formed on the grayscale image based on the calculation of one of the five kinds of the retrieving method, i.e. the moving variance retrieving method, the contrast retrieving method, the distance retrieving method, the gradient EWMA difference retrieving method, and the angle retrieving method, the time spent in calculation of the tumor contour of the image processing system can be minimized, and the similarity of the tumor contour compared with the actual contour of the tumor is maximized.

In the method for retrieving a tumor contour of an image processing system that includes a memory storing a grayscale image and a processor according to the first embodiment of the present invention, each of the plurality of reference segments includes a plurality of local segments and each of the plurality of local segments includes a plurality of moving horizons, wherein each of the plurality of local segments consists of one of the plurality of measured points, at least one measured point before and at least one measured point after the one of the plurality of measured points. Besides, each of the plurality of moving horizons consists of one of the plurality of measured points in the corresponding local segment and at least one measured point after the one of the plurality of measured points.

Moreover, the tumor contour suggestion point can be retrieved by a moving variance retrieving method comprising the steps of: calculating a gradient variance of the grayscale image in the plurality of local segments and an average gradient variance of the grayscale image in the plurality of moving horizons; calculating the ratio of the gradient variance of the grayscale image in the plurality of local segments to the average gradient variance of the grayscale image in the plurality of moving horizons; and retrieving the measured point corresponding to the maximum ratio as the tumor contour suggestion point.

In the method for retrieving a tumor contour of an image processing system that includes a memory storing a grayscale image and a processor according to the first embodiment of the present invention, a center of gravity of the input tumor contour is retrieved and a plurality of contrast reference segments is defined. Besides, each of the plurality of contrast reference segments extends from the center of the gravity to of the corresponding reference segments, respectively.

Moreover, the tumor contour suggestion point can be retrieved by a contrast retrieving method comprising the steps of: calculating gradients of the grayscale image in the plurality of reference segments and an average gradient of the grayscale image in the plurality of contrast reference segments; calculating the differences between the gradients of the grayscale image in the plurality of reference segments and an average gradient of the grayscale image in the plurality of contrast reference segments; and retrieving the measured point corresponding to the maximum difference as the tumor contour suggestion point.

In the method for retrieving a tumor contour of an image processing system that includes a memory storing a grayscale image and a processor according to the first embodiment of the present invention, the tumor contour suggestion point can be retrieved in sequence by a distance retrieving method comprising the steps of: when there are no tumor contour suggestion points before, taking one of the plurality of measured points on the first reference segment as a first point, or when there is one tumor contour suggestion point before, taking a last tumor contour suggestion point on one of the plurality of reference segments as the first point; taking one of the plurality of measured points on the next reference segment as a second point; and retrieving the measured point on the next reference segment, having the minimum distance between the first point and the second point as the tumor contour suggestion point on the next reference point.

In the method for retrieving a tumor contour of an image processing system that includes a memory storing a grayscale image and a processor according to the first embodiment of the present invention, the tumor contour suggestion point can be retrieved in sequence by a gradient EWMA difference retrieving method comprising the steps of: when there are no tumor contour suggestion points before, taking one of plurality of measured points on the first reference segment as a reference list; or when there is one tumor contour suggestion point before, taking all of the pervious tumor contour suggestion points as the reference list; providing an EWMA weighting formula; determining the weighting factor of the EWMA weighting formula and receiving the EWMA value of the reference list by the gradients of grayscale image of each of the measured points or the tumor contour suggestion points in the reference list; using the EWMA value of the reference list and the gradients of grayscale image of each of the plurality of measured points on the next reference segment as the input variables of the EWMA weighting formula; defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment.

In the method for retrieving a tumor contour of an image processing system that includes a memory storing a grayscale image and a processor according to the first embodiment of the present invention, the tumor contour suggestion point can be retrieved in sequence by an angle retrieving method comprising the steps of: when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point; defining a vector going from the first point to the second point as a first vector, and vectors going from the second point to each of the plurality of measured points on a next reference segment as a plurality of second vectors; calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

Other objects, advantages, and novel features of the invention will become more apparent from the following detailed description when taken in conjunction with the accompanying drawings.

BRIEF DESCRIPTION OF THE DRAWINGS

FIG. 5 is a flowchart displaying the moving variance retrieving method for retrieving the tumor contour suggestion point.

FIG. 9 is a flowchart displaying the contrast retrieving method for retrieving the tumor contour suggestion point.

FIG. 10 is a flowchart displaying the distance retrieving method for retrieving the tumor contour suggestion point.

FIG. 11 is a flowchart displaying the gradient EWMA difference retrieving method for retrieving the tumor contour suggestion point.

FIG. 12 is a flowchart displaying the angle retrieving method for retrieving the tumor contour suggestion point.

DETAILED DESCRIPTION OF THE PREFERRED EMBODIMENT

Figure 1:
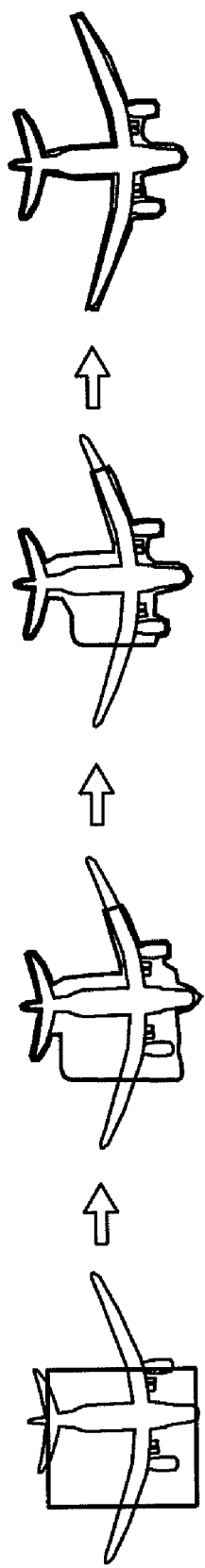
FIG. 1 is combination of schematic views of the process for retrieving contour of airplanes according to Snake algorithm.
Figure 2:
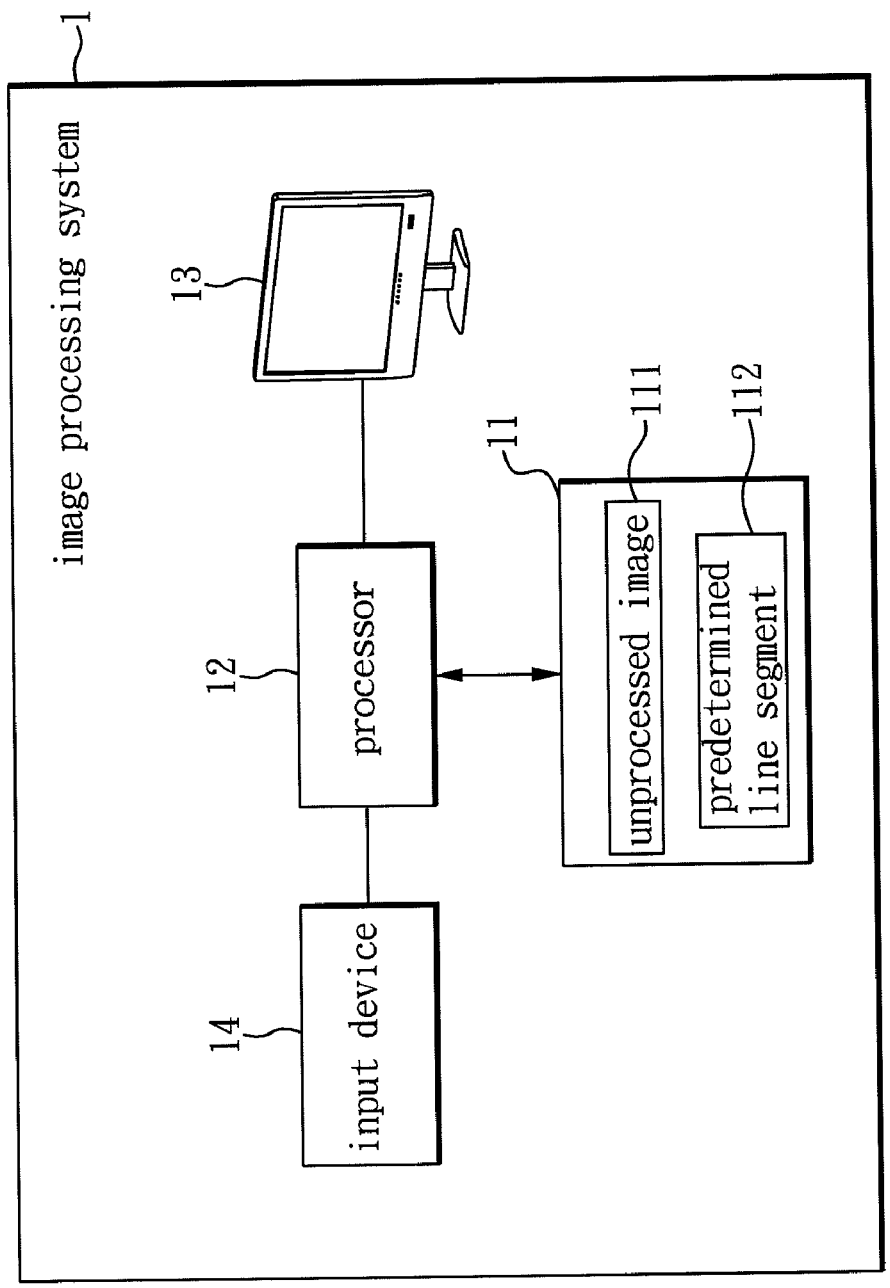
FIG. 2 is a system configuration diagram according to a preferred example of the present invention.
Figure 3:
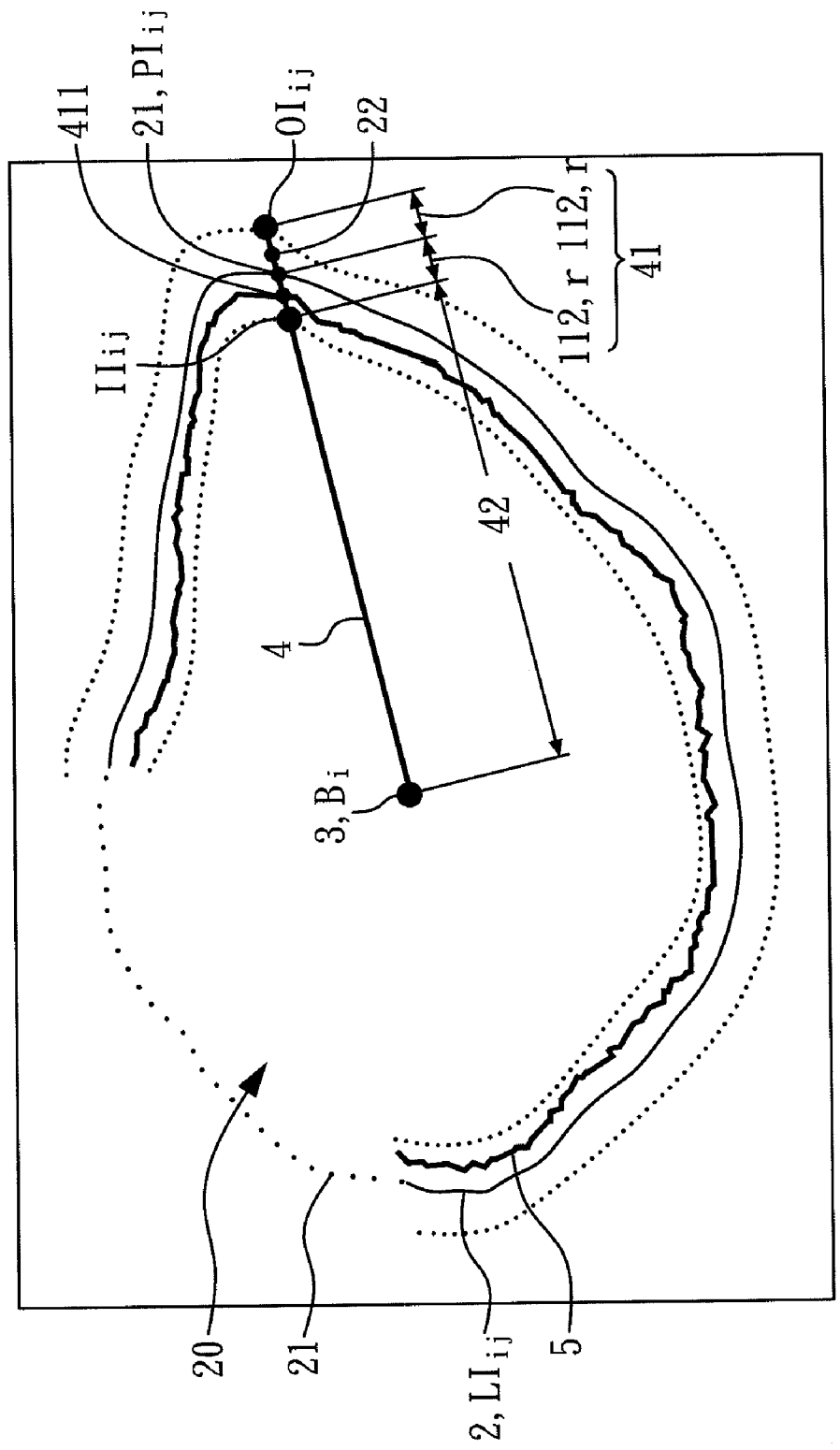
FIG. 3 is a schematic diagram for showing a tumor contour retrieving method according to a preferred example of the present invention.

Please refer to FIGS. 2 and 3. FIG. 2 shows a system configuration diagram for illustrating a method for retrieving a tumor contour for an image processing system according to a preferred example of the present invention. FIG. 3 is a schematic diagram for showing a method for retrieving a tumor contour for an image processing system according to a preferred example of the present invention.

As shown in FIG. 2, the image processing system 1 includes a memory 11, a processor 12, a display screen 13 and an input device 14. The memory 11 can store an unprocessed image 111 and a predetermined line segment 112. Herein, the unprocessed image 111 means an ultrasound image without being processed by the method for retrieving a tumor contour according to the present invention, and can be input through the input device 14. Furthermore, FIG. 3 shows a tumor region 20. The processed image can be output through the display screen 13.

Figure 4:
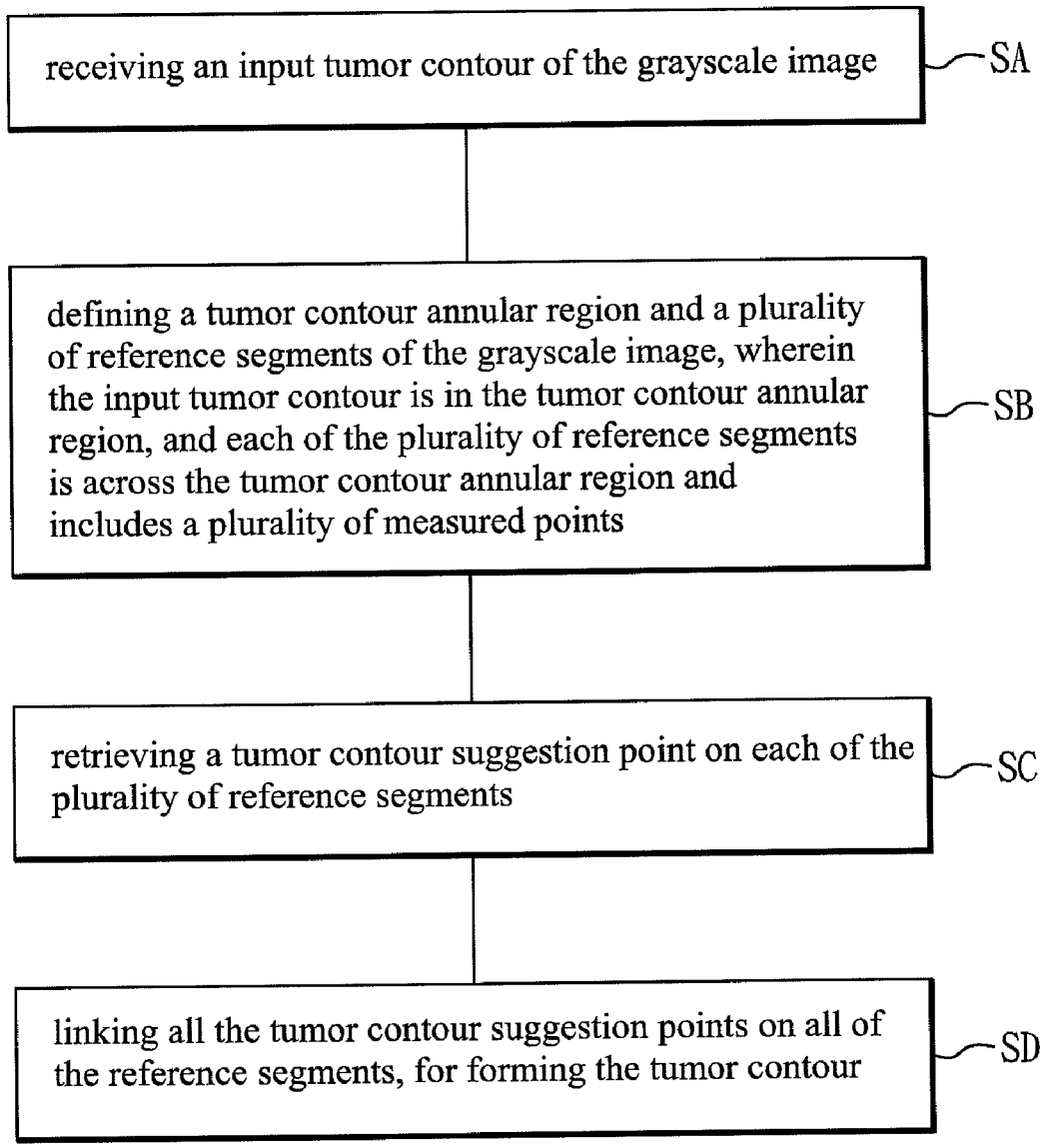
FIG. 4 is a flowchart of the method for retrieving a tumor contour of an image processing system according to the first embodiment of the present invention.

Please refer to FIG. 4, which is a flowchart of the method for retrieving a tumor contour of an image processing system according to the first embodiment of the present invention. The method for retrieving a tumor contour for an image processing system that includes a memory storing a grayscale image and a processor according to the first embodiment of the present invention comprises:

Step SA: receiving an input tumor contour of the grayscale image;

Step SB: defining a tumor contour annular region and a plurality of reference segments of the grayscale image, wherein the input tumor contour is in the tumor contour annular region, and each of the plurality of reference segments is across the tumor contour annular region and includes a plurality of measured points;

Step SC: retrieving a tumor contour suggestion point on each of the plurality of reference segments; and Step SD: linking all the tumor contour suggestion points on all of the reference segments, for forming the tumor contour.

First, in Step SA, an input tumor contour 2 consisting of plural input contour points 21 is input on an unprocessed image 111. A user or a doctor can input the input tumor contour 2 by roughly rather than accurately hand-drawing the tumor contour. Herein, the input tumor contour 2 represented by $LI_i$ consists of input contour points 21, in which the number of the input contour points 21 is represented by $n_i$ (i=1, 2, ..., n; i, n∈N). In addition, the jth input contour point 21 of the ith input tumor contour 2 is represented by $PI_{ij}=(^xPI_{ij}, ^yPI_{ij})(LI_i=\{PI_{i1}, PI_{i2}, ..., PI_{ij}\}, j=1, 2, ..., n_i, j∈ N)$.

Subsequently, in Step SB, both a tumor contour annular region and a plurality of reference segments of the grayscale image are defined. Besides, the input tumor contour is in the tumor contour annular region, and each of the plurality of reference segments is across the tumor contour annular region and includes a plurality of measured points. For instance, a gravity center 3 of the input tumor contour 2 is retrieved. Herein, the gravity center 3 of the ith input tumor contour (i.e. the gravity center 3 of all $PI_{ij}$) is represented by $B_i$, as shown in the formula (1-1).

$$B_i = \left( \left[ \frac{\sum_{j=1}^{n_i} x_{PI_{ij}}}{n_i} \right], \left[ \frac{\sum_{j=1}^{n_i} y_{PI_{ij}}}{n_i} \right] \right) \quad (1\text{-}1)$$

Next, the gravity center 3 and each input contour point 21 are linked individually through an extended line, and thereby plural reference lines 4 are defined. Then, a reference segment 41 containing its corresponding input contour point 21 is retrieved from each of the plural reference lines 4 (Step SB). In detail, the reference segment 41 is determined from each of the reference lines 4 by defining the predetermined line segment 112 at the directions towards and away from the gravity center 3 with respect to the input contour point 21 as a basis point. The predetermined line segment 112 determines the length of the reference segment 41 and directly affects the processing time and accuracy.

In other words, the input contour point 21 is taken as a basis point, and the predetermined line segment 112 is used as a radius being a specific physical distance from the input contour point 21. The predetermined line segment 112 is represented by $r$ (r∈N). $\overrightarrow{B_iPI_{ij}}$ is a line that links the gravity center 3 and the jth input contour point 21 of the ith input tumor contour 2. The jth input contour point 21 is used as a center and then a circle with a specific radius (i.e. the predetermined line segment 112, r) can be formed. The circle and the line $\overrightarrow{B_iPI_{ij}}$ cross at two points, an outer crosspoint $OI_{ij}=(^xOI_{ij}, ^yOI_{ij})$ and an inner crosspoint $II_{ij}=(^xII_{ij}, ^yII_{ij})$. The jth reference segment 41 corresponding to the jth input contour point 21 of the ith input tumor contour 2 is the line $\overline{OI_{ij}II_{ij}}$, containing the measured points 22 of which the number is $a_{ij}$. The jth reference line segment 42 is the line $\overline{B_iII_{ij}}$. Herein, $a_{ij}$, $h_{ij}$ ∈ N and $a_{ij} \leq 2r+1$.

Then, in Step SC, a tumor contour suggestion point 441 is retrieved from each reference segment 41.

At final, by linking all the tumor contour suggestion points on all of the reference segments, the tumor contour is thus formed (Step SD).

EXAMPLE 1

In this example, the step SC of the method for retrieving a tumor contour of an image processing system that includes a memory storing a grayscale image and a processor according to the first embodiment of the present invention, the tumor contour suggestion point on each of the plurality of reference segments can be retrieved by a moving variance retrieving method. As shown in FIG. 5, the moving variance retrieving method comprises the steps of:

calculating a gradient variance of the grayscale image in the plurality of local segments and an average gradient variance of the grayscale image in the plurality of moving horizons;

calculating the ratio of the gradient variance of the grayscale image in the plurality of local segments to the average gradient variance of the grayscale image in the plurality of moving horizons; and retrieving the measured point corresponding to the maximum ratio as the tumor contour suggestion point.

Moreover, in the above-mentioned moving variance retrieving method, each of the plurality of reference segments includes a plurality of local segments and each of the plurality of local segments includes a plurality of moving horizons, wherein each of the plurality of local segments consists of one of the plurality of measured points, at least one measured point before and at least one measured point after the one of the plurality of measured points. Besides, each of the plurality of moving horizons consists of one of the plurality of measured points in the corresponding local segment and at least one measured point after the one of the plurality of measured points.

In this example, moving variance is applied to observe the value variance of the entire region caused by the value variance around a partial segment of the entire region. Moving variance applied in the present invention is a primary index of features. Through moving variance applied in the first example, the tumor contour suggestion point can be directly obtained from the reference segment 41 by algorithm.

With reference to FIGS. 3 and 5, each reference segment 41 contains a plurality of measured points 22, a plurality of local segments and a plurality of moving horizons. In the present example, the plural measured points mean plural image pixel points. Each of the plural local segments consists of one of the plural measured points 22, the former one or more measured points 22, and the latter one or more measured points 22. Each of the plural moving horizons consists of one of the plural measured point 22 and the latter one or more measured points 22 in the corresponding plural local segments.

That is, in the case that the number of points in the former/latter segment with respect to $AI_{ijk}$ on the reference segment 41 (i.e. $\overline{OI_{ij}II_{ij}}$) is p, the segment containing (2×p+1) image pixel points is called a local segment. Since each point on the reference segment 41 has a local segment, the number of measured points on the reference segment 41 is equal to that of the local segments. Regarding moving horizons, in the case that the number of $AI_{ijk}$ in the local segment plus the latter points is q, since the local segment contains (2×p+1) image pixel points, there are (2×p+1−(q−1)=2×p−q+2) horizons. Herein, each horizon containing q image pixel points is called a moving horizon.

However, the method for retrieving a tumor contour suggestion point 411 according to Example 1 of the present invention is carried out as follows. First, the gradient variances of the grayscale images in the plural local segments and the average gradient variance of the grayscale images in the plural moving horizons are respectively calculated. Then, the ratios of the gradient variances of the grayscale images in the plural local segments to the average gradient variance of the grayscale images in the plural moving horizons are respectively calculated. Subsequently, the measured point 22 corresponding to the maximum ratio is retrieved as a tumor contour suggestion point 411.

Figure 6:
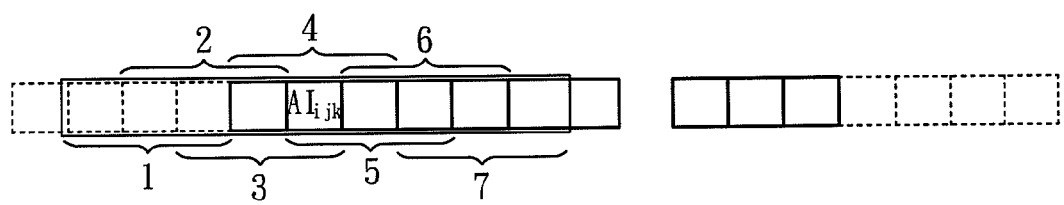
FIG. 6 is a schematic view for showing the local segments and the moving horizons according to Example 1 of the present invention.

In the case of the image pixel values in the kth local segment on the reference segment 41 ($\overline{OI_{ij}II_{ij}}$) being $G_{ijk-p}$, $G_{ijk-p+1}$, ..., $G_{ijk+p-1}$, $G_{ijk+p}$, the gradient variance of the grayscale image in the local segment is represented by $RL_{ijk}$ ($RL_{ijk}$=varp[$G_{ijk-p}$, $G_{ijk+p}$], p∈N). Since the local segment containing the former and latter points with respect to $AI_{ijk}$ may be beyond the range of the reference segment 41 (i.e. $\overline{OI_{ij}II_{ij}}$), extended auxiliary points, before and after the original reference segment 41, should be formed so as to observe the gradient variance of the grayscale images of all points in the local segment. In detail, with reference to FIG. 6, there is a schematic view to show the local segments and the moving horizons according to Example 1 of the present invention. The squares with continuous lines mean measured points 22 on the reference segment 41, and the squares with dashed lines mean the extended auxiliary points. In addition, the red square frame is $AI_{ijk}$ point, the red rectangular frame is a local segment corresponding to $AI_{ijk}$ point, and the brackets are moving horizons. As shown in FIG. 6, in the case of k=2, p=4 and q=3, the local segment corresponding to the second measured point on the reference segment contains (2×4+1=9) points, and (4−3+2=7) moving horizons.

In the case of the image pixel values in the gth moving horizon on the local segment being $G_{ijk-p+g-1}$, $G_{ijk-p+g}$, ..., $G_{ijk-p+g+q-1}$, $G_{ijk-p+g\pm q-2}$, the gradient variance of the grayscale image in the moving horizon is represented by $RM_{ijkg}$ ($RM_{ijkg}$=varp[$G_{ijk-p+g-1}$, $G_{ijk-p+g+q-2}$]). The average gradient variance of the grayscale images in the moving horizons is represented by $\overline{RM_{ijk}}$, as shown in the formula (1-2).

$$\overline{RM_{ijk}} = \frac{\sum_{g=1}^{2\times p-q+2} RM_{ijkg}}{2\times p - q + 2} \quad (1\text{-}2)$$

Herein, q, g∈N. In order to allow a local segment to have two or more moving horizons, q≦2×p−1.

Moreover, the moving variance of $AI_{ijk}$ on the measures line 41 ($\overline{OI_{ij}II_{ij}}$) is defined as the ratio of $RL_{ijk}$ (the gradient variance of the grayscale image in the local segment corresponding to $AI_{ijk}$) to $\overline{RM_{ijk}}$ (the average gradient variance of the grayscale images in the moving horizons of the local segment), represented by $MV_{ijk}$, as shown in the formula (1-3).

$$MV_{ijk} = \frac{RL_{ijk}}{\overline{RM_{ijk}}} \quad (1\text{-}3)$$

Herein, the larger the value of $MV_{ijk}$ is, the higher the possibility of the point being the tumor contour suggestion point is. If q=1, the moving variance does not regard the moving horizon ($MV_{ijk}=RL_{ijk}$).

Figure 7:
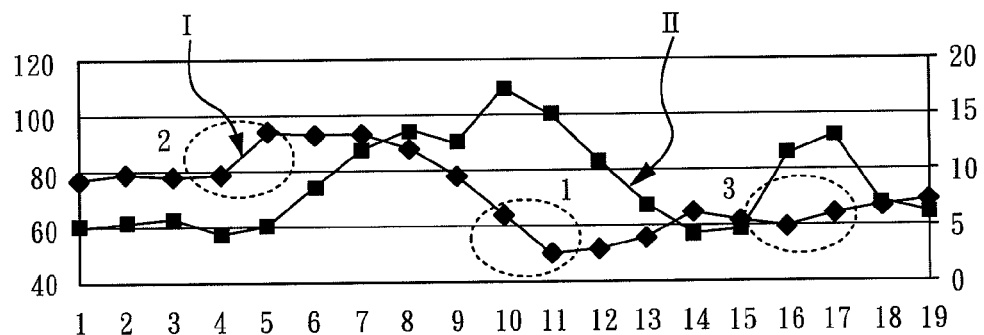
FIG. 7 is a line chart for showing the gradients of the grayscale images and corresponding moving variances of all points on the reference segment according to Example 1 of the present invention.

Hereafter, the application of moving variance in the present invention will be illustrated. Please refer to Table 1 and FIG. 7. Table 1 shows the gradients of the grayscale images and moving variances of points on the reference segment according to Example 1 of the present invention, in which the parameters p and q are set as 5 and 2, respectively. In Table 1, the serial number k of each measured point 22 is shown in the first column, the gradient $G_{ijk}$ of the grayscale image of each measured point 22 is shown in the second column, and $MV_{ijk}$ of each measured point 22 is shown in the third column. FIG. 7 is a line chart displaying the gradients of the grayscale images and corresponding moving variances of all points on the reference segment according to Example 1 of the present invention. Herein, the line I for the gradients of the grayscale images and the line II for the moving variances can indicate that various gradients of grayscale images produce various moving variances due to surrounding variance.

Figure 8:
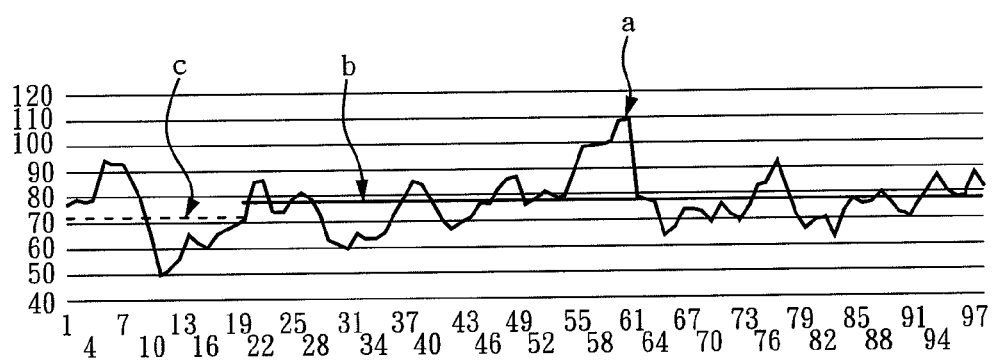
FIG. 8 is a gradient cross-sectional view of grayscale images of the tumor from the gravity center of the tumor to the outer crosspoint on the reference segment.

Meanwhile, with reference to FIG. 8, there is a gradient cross-sectional view of grayscale images of the tumor from the gravity center of the tumor to the outer crosspoint on the reference segment. Herein, the line a shows the gradients of the grayscale images, the line b shows the average gradient of the grayscale images of the reference segment 41, and the line c shows the average gradient of the grayscale images of the reference line segment 42. FIG. 8 indicates that the average gradient of the grayscale images of the reference segment 41 is smaller than that of the reference line segment 42 owing to low-echogenic ring. In FIG. 7, the three locations where the gradient variances of the grayscale images are larger on the reference segment 41 are circled. In the term of the moving variances, the $10^{th}$ point according to the circle 1 is the largest, the $11^{th}$ point is larger than the $8^{th}$ point, and the $17^{th}$ point is the smallest.

Additionally, regarding the gradient cross-sectional view of grayscale images of the tumor from the gravity center of the tumor to the outer crosspoint on the reference segment 41 (FIG. 8), it can be found that the values from the $7^{th}$ point to the $20^{th}$ point are shown in a concave line, which is lower than the average gradient of the grayscale images of the reference line segment. This concave line corresponds to the low-echogenic ring of the ultrasound image. Moreover, although the gradient variance of the grayscale images in the circle 2 is large, the moving variance according to the circle 2 is lower than those according to the circles 1 and 3 due to the gradients of the surrounding images. Based on moving variances, the best suggestion point on the reference segment is the $10^{th}$ point than the $11^{th}$ point, the $8^{th}$ point and the $17^{th}$ point.

TABLE 1

| k | 1 | 2 | 3 | 4 | 5 |
|---|---|---|---|---|---|
| $G_{ijk}$ | 77 | 79 | 78 | 79 | 94 |
| $MV_{ijk}$ | 4.996216 | 5.431265 | 5.72553 | 4.359829 | 5.065877 |
| k | 6 | 7 | 8 | 9 | 10 |
| $G_{ijk}$ | 93 | 93 | 88 | 78 | 64 |
| $MV_{ijk}$ | 8.586214 | 11.91848 | 13.55545 | 12.59645 | 17.43012 |
| k | 11 | 12 | 13 | 14 | 15 |
| $G_{ijk}$ | 50 | 52 | 56 | 65 | 62 |
| $MV_{ijk}$ | 14.88913 | 10.87886 | 6.907269 | 4.268695 | 4.830066 |
| k | 16 | 17 | 18 | 19 | |
| $G_{ijk}$ | 60 | 65 | 67 | 69 | |
| $MV_{ijk}$ | 11.60418 | 13.1099 | 7.002381 | 6.10648 | |

EXAMPLE 2

In this example, the step SC of the method for retrieving a tumor contour of an image processing system that includes a memory storing a grayscale image and a processor according to the first embodiment of the present invention, the tumor contour suggestion point on each of the plurality of reference segments can be retrieved by a contrast retrieving method. As shown in FIG. 9, the contrast retrieving method comprises the steps of:

calculating gradients of the grayscale image in the plurality of reference segments and an average gradient of the grayscale image in the plurality of contrast reference segments;

calculating the differences between the gradients of the grayscale image in the plurality of reference segments and an average gradient of the grayscale image in the plurality of contrast reference segments; and retrieving the measured point corresponding to the maximum difference as the tumor contour suggestion point.

Moreover, in the above-mentioned contrast retrieving method, a center of gravity of the input tumor contour is retrieved and a plurality of contrast reference segments is defined. Besides, each of the plurality of contrast reference segments extends from the center of the gravity to of the corresponding reference segments, respectively.

In this example of the present invention, the contrast principle is applied to assign the location of a tumor from an ultrasound image through naked eyes. Based on the center of the tumor, the tumor boundary can be discriminated through the gradient variance of the grayscale images from the center of the tumor to the probable boundary and the region around the boundary, in addition to the low-echogenic ring in the ultrasound image caused by spongy inflammation due to compression and infiltration between the tumor and tissues around the tumor. Thereby, the contrast principle refers to that the degree of visional difference between each point in a range and the desired region is observed. Contrast applied in the present invention is a primary index of features. Through the contrast method applied in the second example of the present invention, the tumor contour suggestion point can be directly obtained from the reference segment 41 by algorithm.

With reference to FIGS. 3 and 9, each reference segment 41 contains a plurality of measured points 22, and each of the plural reference lines 4 contains a reference line segment 42. The reference line segment 42 is from the gravity center 3 to the end of the reference segment 41 closer to the gravity center 3. However, the method for retrieving the tumor contour suggestion point 411 according to Example 2 of the present invention is carried out as follows. First, the gradients of the grayscale images of the plural measured points 22 and the average gradient of the grayscale images in the reference line segment 42 are respectively calculated. Next, the differences between the gradients of the grayscale images of the plural measured points 22 and the gradient average of the grayscale images in the reference line segment of the corresponding reference line 4 are respectively calculated. Then, the measured point 22 corresponding to the maximum difference is retrieved as a tumor contour suggestion point 411.

Herein, the average gradient of the grayscale images in the reference line segment 42 ($\overline{B_iII_{ij}}$) is represented by $\overline{G_{ijl}}$, as shown in the formula (2-1).

$$\overline{G_{ijl}} = \frac{\sum_{l=1}^{h_{ij}} G_{ijl}}{h_{ij}} \quad (2-1)$$

In addition, the contrast of the point $AI_{ijk}$ on the reference segment 41 ($\overline{OI_{ij}II_{ij}}$) is defined as the difference between the gradient of the grayscale image of such point and the average gradient ($\overline{G_{ijl}}$) of the grayscale images on the reference line segment 42 ($\overline{B_iII_{ij}}$) corresponding to such point, represented by $C_{ijk}$ ($C_{ijk}=|G_{ijk}-\overline{G_{ijl}}|$). The larger $C_{ijk}$ is, the higher the possibility of the point being the tumor contour suggestion point 411 is.

Hereafter, the application of the contrast principle in the present invention will be explained through data. Please refer to Table 2. Table 2 shows the gradients of the grayscale images and contrast of points on the reference segment according to Example 2 of the present invention, in which the average gradient of the grayscale images in the reference line segment 42 is 77.4. In Table 2, the serial number k of each measured point 22 on the reference segment 41 ($\overline{OI_{ij}II_{ij}}$) is shown in the first column, the gradient $G_{ijk}$ of the grayscale image of each measured point 22 is shown in the second column, and $C_{ijk}$ of each measured point 22 is shown in the third column. The average gradient of the grayscale image s in the reference line segment 42 ($\overline{B_iII_{ij}}$) in Table 2 is 77.4.

Accordingly, through Table 2, it can be known that the 11$^{th}$ point is the largest, the 12$^{th}$ point is larger than the 13$^{th}$ point and the 16$^{th}$ point is the smallest, in the term of contrast. Please refer to FIG. 7 together with Table 2. Although the 5$^{th}$ point in the circle 2 presents the largest gradient of the grayscale image and the gradient variance of the grayscale images in the circle 2 is large, the gradient of the grayscale image in the circle 2 is closer to the average gradient of the grayscale images in the reference line segment. Thereby, the contrast at the 5$^{th}$ point in the circle 2 is lower than those at the 11$^{th}$ point in the red circle 1 and the 16$^{th}$ point in the circle 3. Based on contrast, the best suggestion point on the reference segment 41 is the 11$^{th}$ point than the 12$^{th}$ point, the 13$^{th}$ point and the 16$^{th}$ point.

TABLE 2

| k | 1 | 2 | 3 | 4 | 5 |
|---|---|---|---|---|---|
| $G_{ijk}$ | 77 | 79 | 78 | 79 | 94 |
| $C_{ijk}$ | 0.4 | 1.6 | 0.6 | 1.6 | 16.6 |
| k | 6 | 7 | 8 | 9 | 10 |
| $G_{ijk}$ | 93 | 93 | 88 | 78 | 64 |
| $C_{ijk}$ | 15.6 | 15.6 | 10.6 | 0.6 | 13.4 |
| k | 11 | 12 | 13 | 14 | 15 |
| $G_{ijk}$ | 50 | 52 | 56 | 65 | 62 |
| $C_{ijk}$ | 27.4 | 25.4 | 21.4 | 12.4 | 15.4 |
| k | 16 | 17 | 18 | 19 | |
| $G_{ijk}$ | 60 | 65 | 67 | 69 | |
| $C_{ijk}$ | 17.4 | 12.4 | 10.4 | 8.4 | |

EXAMPLE 3

In this example, the step SC of the method for retrieving a tumor contour of an image processing system that includes a memory storing a grayscale image and a processor according to the first embodiment of the present invention, the tumor contour suggestion point on each of the plurality of reference segments can be retrieved in sequence by a distance retrieving method. As shown in FIG. 10, the distance retrieving method comprises the steps of:

when there are no tumor contour suggestion points before, taking one of the plurality of measured points on the first reference segment as a first point, or when there is one tumor contour suggestion point before, taking a last tumor contour suggestion point on one of the plurality of reference segments as the first point; taking one of the plurality of measured points on the next reference segment as a second point; and retrieving the measured point on the next reference segment, having the minimum distance between the first point and the second point as the tumor contour suggestion point on the next reference point.

In this example, the distance is used as the main consideration wherein the distance between two suggestion points respectively selected from two reference segments 41 are considered. In detail, after a former suggestion point is selected from the former reference segment 41, the distances from the former suggestion point to each measured point selected from the later reference segment 41 are considered. The physical meaning of the aforesaid is that the distance from the later suggestion point to the former suggestion point should be shorter than that of other measured points to the former suggestion point. The distance used in the present invention is an auxiliary index of features. In other words, a former suggestion point requires to be indicated, and then the algorithm is performed to retrieve a later suggestion data point selected from the later reference segment 41.

With reference to FIGS. 3 and 10, at first, based on the method of moving variance described in Example 1, at least one initial suggestion point 411 is retrieved from the contour. Then, the initial suggestion point 411 is used as a reference point, and a point retrieved from the reference line 4 and nearest to the initial suggestion point 411 with a minimum linear distance, is used as a subsequent suggestion point. Other suggestion points are retrieved from other reference segments in the abovementioned manner.

Besides, the distant of the point $AI_{ijk}$ on the reference segment 41 ($\overline{OI_{ij}II_{ij}}$) is defined as the physical distance ($D_{ijk}$) from the measured point 22 to the initial suggestion point 411. The relation of the above-mentioned parameters is shown as the following formula 3-1.

$$D_{ijk} = \sqrt{(x_{PS_{ij'-1}} - x_{AI_{ijk}})^2 + (y_{PS_{ij'-1}} - y_{AI_{ijk}})^2} \quad \text{(formula 3-1)}$$

Since the measured point 22 on the first reference segment 41 has no former reference point for calculation, j is 2 or more. As $D_{ijk}$ decreases, the possibility of the point to be the desirable suggestion point 411 increases.

The following description explains the effect of the distance applied in the present invention by actual data. With reference to the following Table 3, Table 3 shows the conversion from the image coordinate of each point on the reference segment of the present example to the distance, where the coordinates of the initial suggestion point in the image is (237, 193). In the first row of Table 3, k is the number of each measured point 22 on the reference segment $\overline{OI_{ij+1}II_{ij+1}}$. The second and third rows show the coordinate ($^xAI_{ij+1k}$, $^yAI_{ij+1k}$) of each measure point 22. Furthermore, the fourth row shows the corresponding $D_{ij+1k}$ of each measured point 22. In Table 3, the corresponding suggestion point is the initial suggestion point (237,193) on the reference line $\overline{B_iII_{ij}}$ obtained by the moving variance. As listed in Table 3, the points 10 and 11 show the shortest distance, and the following are the points 12, 9, and 13 in order.

Another reason why the distance value is an auxiliary index of features is that the result of retrieving the former suggestion point dramatically affects the corresponding distance of each point on the later reference segment and the result of retrieving the later suggestion point. For example, when the values of $MV_{ijk}$ and $C_{ijk}$ are used, although two suggestion points locating on distinct sites and having difference distances are probably retrieved respectively from the neighboring two reference segments, $D_{ijk}$ is supposed to affect the neighboring two reference segments and then two suggestion points close to each other are retrieved.

TABLE 3

| k | 1 | 2 | 3 | 4 | 5 |
|---|---|---|---|---|---|
| $x_{AI_{ij+1k}}$ | 227 | 228 | 229 | 230 | 231 |
| $y_{AI_{ij+1k}}$ | 196 | 195 | 195 | 195 | 194 |
| $D_{ij+lk}$ | 10.440 | 9.220 | 8.246 | 7.280 | 6.083 |
| k | 6 | 7 | 8 | 9 | 10 |
| $x_{AI_{ij+1k}}$ | 232 | 233 | 234 | 235 | 236 |
| $y_{AI_{ij+1k}}$ | 194 | 194 | 193 | 193 | 193 |
| $D_{ij+lk}$ | 5.099 | 4.123 | 3.000 | 2.000 | 1.000 |
| k | 11 | 12 | 13 | 14 | 15 |
| $x_{AI_{ij+1k}}$ | 237 | 238 | 239 | 240 | 241 |
| $y_{AI_{ij+1k}}$ | 192 | 192 | 192 | 191 | 191 |
| $D_{ij+lk}$ | 1.000 | 1.414 | 2.236 | 3.606 | 4.472 |
| k | 16 | 17 | 18 | 19 | |
| $x_{AI_{ij+1k}}$ | 242 | 243 | 244 | 245 | |
| $y_{AI_{ij+1k}}$ | 191 | 190 | 190 | 190 | |
| $D_{ij+lk}$ | 5.385 | 6.708 | 7.616 | 8.544 | |

EXAMPLE 4

In this example, the step SC of the method for retrieving a tumor contour of an image processing system that includes a memory storing a grayscale image and a processor according to the first embodiment of the present invention, the tumor contour suggestion point on each of the plurality of reference segments can be retrieved in sequence by a gradient EWMA difference retrieving method. As shown in FIG. 11, the gradient EWMA difference retrieving method comprises the steps of:

when there are no tumor contour suggestion points before, taking one of plurality of measured points on the first reference segment as a reference list; or when there is one tumor contour suggestion point before, taking all of the pervious tumor contour suggestion points as the reference list;

providing an EWMA weighting formula;

determining the weighting factor of the EWMA weighting formula and receiving the EWMA value of the reference list by the gradients of grayscale image of each of the measured points or the tumor contour suggestion points in the reference list;

using the EWMA value of the reference list and the gradients of grayscale image of each of the plurality of measured points on the next reference segment as the input variables of the EWMA weighting formula;

defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment.

In this example, the gradient exponentially weighted moving average difference (gradient EWMA difference) between the grayscale images is used as the main consideration. EWMA is a statistic of a moving average with memory, and is weighed based on the importance of the historical data valued by the programmer. Therefore, older historical data may be placed with more or less importance by EWMA. In detail, the concept is to consider the gradient EWMA difference between the grayscale images of the neighboring two suggestion points. The physical meaning of the aforesaid description is that the gradient EWMA difference between the grayscale images of the former and later suggestion points should be less than that between the grayscale images of other measured points and the former suggestion point. The gradient EWMA difference between the grayscale images also belongs an auxiliary index of features. In other words, a former suggestion point requires to be indicated, and then the algorithm is performed to retrieve a later suggestion data point selected from the later reference segment 41.

With reference to FIGS. 3 and 11, each of the reference segments 41 includes a plurality of measured points 22. Basically, the method for retrieving a suggestion point 411 from the contour is described as follows. First, based on the method of moving variance described in Example 1, at least one initial suggestion point 411 is retrieved from the contour. Then, the gradient of the grayscale images of the measured points 22 and the EWMA of at least one initial suggestion point 411 are respectively calculated. Subsequently, the differences between the gradient of the grayscale images of the measured points 22 and the EWMA of at least one initial suggestion point 411 are calculated. The minimal difference is chosen, and the corresponding measured point 22 is retrieved as a suggestion point 411. Other suggestion points are retrieved from other reference segments in the abovementioned manner.

Basically, the EWMA of the point $AI_{ijk}$ on the reference segment 41 ($\overline{OI_{ij}II_{ij}}$) is defined as the weight-interpolated value ($Z_{ijk}$), which is obtained from the gradient of the grayscale image of the measured point 22 and the EWMA of the former suggestion point. The EWMA of the reference segment $\overline{OI_{ij}II_{ij}}$ obtained from the aforesaid method for retrieving the former suggestion point is represented by $Z_{ij'}$. The relation of the abovementioned variants is shown as the following formula 4-1.

$$Z_{ijk} = \lambda G_{ijk} + (1-\lambda) Z_{ij'-1}, \quad 0 < \lambda \leq 1 \qquad \text{(formula 4-1)}$$

Since the measured point on the first reference segment has no former reference point for calculation, $Z_{i1k}$ is equal to $Z_{i1}$ and $G_{i1}$.

The following formula illustrates that the weighting adjustment of the EWMA will affect the importance of the historical data.

$$\begin{aligned} Z_{ijk} &= \lambda G_{ijk} + (1-\lambda) Z_{ij'-1} \\ &= \lambda G_{ijk} + (1-\lambda)[\lambda G_{ij'-1} + (1-\lambda) Z_{ij'-2}] \\ &= \ldots \\ &= \lambda G_{ijk} + \lambda(1-\lambda) G_{ij'-1} + \lambda(1-\lambda)^2 G_{ij'-2} + \ldots + \\ &\quad \lambda(1-\lambda)^{(j'-1)} G_{i2} + (1-\lambda)^{j'} G_{i1} \\ &= \lambda G_{ijk} + \sum_{z=1}^{j'-2} \lambda(1-\lambda)^z G_{i(j'-z)} + (1-\lambda)^{j'} G_{i1} \end{aligned}$$

In the formula, as $\lambda$ increases, it indicates that the neighboring data have more weighting effect to the output data; by contrast, as $\lambda$ decreases, it indicates that the old and new historical data have more similar weighting effect to the output data. For example, when $j=j'=4$, if $\lambda=0.9$, $Z_{i4k}$ can be shown as $Z_{i4k}=0.9G_{i4k}+0.09G_{i3}+0.009G_{i2}+0.001G_{i1}$. This indicates $Z_{i4k}$ is greatly affected by $G_{i4k}$. By contrast, if $\lambda=0.1$, $Z_{i4k}$ can be shown as $Z_{i4k}=0.1G_{i4k}+0.09G_{i3}+0.081G_{i2}+0.729G_{i1}$. It can be seen that $G_{i2}$, $G_{i3}$, and $G_{i4k}$ similarly affect $Z_{i4k}$.

Moreover, the gradient EWMA difference of the grayscale images means that the gradient EWMA difference of the point $AI_{ijk}$ is on the reference segment 41 ($\overline{OI_{ij}II_{ij}}$) and it is defined as the difference ($E_{ijk}$) between the gradient of the grayscale image and the EWMA ($Z_{ijk}$) of the point $AI_{ijk}$. $E_{ijk}=|G_{ijk}-Z_{ijk}|$. As $E_{ijk}$ decreases, the possibility of the point to be the desirable suggestion point increases. Since the measured point on the first reference segment has no former reference point for calculation, j is 2 or more.

The following description explains the effect of the gradient EWMA difference of the grayscale images applied in the present invention by actual data. With reference to the following Table 4, Table 4 shows the conversion from the coordinates of each point (in the image) on the reference segment to the gradient EWMA difference of the grayscale images in the present example, wherein the EWMA of the initial suggestion point is 64. In the first row of Table 4, k is the number of each measured point on the reference segment $\overline{OI_{ij+1}II_{ij+1}}$. The second row shows the gradient ($G_{ij+1k}$) of the grayscale image of each measure point. The third row shows the corresponding $E_{ij+1k}$ of each measure point. In Table 4, the $Z_{ij}$ of the suggestion point is the EWMA ($Z_{ij}$) of the suggestion point on the reference line $\overline{B_iII_{ij}}$ obtained by the moving variance. As listed in Table 4, the points 15, 17, and 18 show the minimum gradient EWMA difference of the grayscale images, and the following are the points 12 and 19 in order.

TABLE 4

| k | 1 | 2 | 3 | 4 | 5 |
|---|---|---|---|---|---|
| $G_{ij+1k}$ | 77 | 81 | 79 | 78 | 92 |
| $E_{ij+1k}$ | 2.6 | 3.4 | 3 | 2.8 | 5.6 |
| k | 6 | 7 | 8 | 9 | 10 |
| $G_{ij+1k}$ | 94 | 93 | 87 | 88 | 78 |
| $E_{ij+1k}$ | 6 | 5.8 | 4.6 | 4.8 | 2.8 |
| k | 11 | 12 | 13 | 14 | 15 |
| $G_{ij+1k}$ | 53 | 50 | 52 | 61 | 65 |
| $E_{ij+1k}$ | 2.2 | 2.8 | 2.4 | 0.6 | 0.2 |
| k | 16 | 17 | 18 | 19 | |
| $G_{ij+1k}$ | 62 | 65 | 65 | 67 | |
| $E_{ij+1k}$ | 0.4 | 0.2 | 0.2 | 0.6 | |

EXAMPLE 5

In this example, the step SC of the method for retrieving a tumor contour of an image processing system that includes a memory storing a grayscale image and a processor according to the first embodiment of the present invention, the tumor contour suggestion point on each of the plurality of reference segments can be retrieved in sequence by an angle retrieving method. As shown in FIG. 12, the angle retrieving method comprises the steps of:

when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point;

defining a vector going from the first point to the second point as a first vector, and vectors going from the second point to each of the plurality of measured points on a next reference segment as a plurality of second vectors;

calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

In this example, the angle is used as the main consideration wherein the relative position of the neighboring three suggestion points is considered. Since the contour of the tumor belongs a continuous curved track, the position and angle differences between the distant of the point $AI_{ijk}$ on the reference segment 41 ($\overline{OI_{ij}II_{ij}}$) and the third suggestion point, should be as small as possible. In other words, using vectors for illustration, the cosine of the included angle between the vectors going from the first to second suggestion points and those going from the second to third suggestion points should be smaller than the cosine of the included angle between the vectors going from the first to second suggestion points and those going from the second suggestion point to the measured point. As the included angle decreases, the cosine thereof (cos θ) increases. Besides, due to cos θ in quadrants I and IV is positive, the continuity required by the contour of the tumor and the minor curvature between the neighboring two suggestion points can be expressed. The angle used in the present invention is an auxiliary index of features. In other words, a former two suggestion points are required, and then the algorithm is performed to retrieve a third suggestion data point selected from the next reference segment.

With reference to FIGS. 3 and 12, each of the reference segments 41 includes a plurality of measured points 22. Basically, the method for retrieving a suggestion point 411 from the contour is described as follows. First, based on the method of moving variance described in Example 1, first and second suggestion points 411 are retrieved from the neighboring two reference segments 41 of the reference line 4. Then, the vector going from the first to second suggestion points, and that going from the second suggestion point to the measured points on the neighboring reference segment 41 are calculated respectively as the first and second vectors. Subsequently, the cosines of the included angle between the first and second vectors are calculated. Among the cosines of the included angle, the maximal cosine is chosen, and the corresponding measured point 22 on the neighboring measure line segment is retrieved as a suggestion point 412. Other suggestion points are retrieved from other reference segments in the abovementioned manner.

Basically, the cosine of the angle of the point $AI_{ijk}$ on the reference segment 41 ($\overline{OI_{ij}II_{ij}}$) is defined as the cosine ($A_{ijk}$) of the included angle between the vectors of $\overline{PS_{ij'-2}PS_{ij'-1}}$ and $\overline{PS_{ij'-1}AI_{ijk}}$. The relationship of the abovementioned parameters is shown as the following formula 5-1.

$$A_{ijk} = \frac{(x_{PS_{ij'-1}} - x_{PS_{ij'-2}})(x_{AI_{ijk}} - x_{PS_{ij'-1}}) + (y_{PS_{ij'-1}} - y_{PS_{ij'-2}})(y_{AI_{ijk}} - y_{PS_{ij'-1}})}{\sqrt{(x_{PS_{ij'-1}} - x_{PS_{ij'-2}})^2 + (y_{PS_{ij'-1}} - y_{PS_{ij'-2}})^2} \sqrt{(x_{AI_{ijk}} - x_{PS_{ij'-1}})^2 + (y_{AI_{ijk}} - y_{PS_{ij'-1}})^2}}$$ (formula 5-1)

As the $A_{ijk}$ increases, the possibility of the point to be the desirable suggestion point increases. Since the measured points on the first and reference segments has no former reference point for calculation, J is 3 or more.

The following description explains the effect of the angle applied in the present invention by actual data. With reference to the following Table 5, Table 5 shows the conversion from the coordinates (in the image) to the angle of each point on the reference segment. The coordinates (in the image) of the suggestion point $PS_{ij'}$ is (237,193), and that of the suggestion point $PS_{ij'+1}$ is (236,193). In the first row of Table 5, k is the number of each measured point on the reference segment $\overline{OI_{ij+2}II_{ij+2}}$. The second and third rows show the coordinate ($^xAI_{ij+2k}, ^yAI_{ij+2k}$)(in the image) of each measure point. The fourth row shows the corresponding $A_{ij+2k}$ of each measure point. In Table 5, the corresponding suggestion point $PS_{ij'}$, on the reference line $\overline{B_iII_{ij}}$ obtained by the moving variance is the coordinate (237,193), and the corresponding suggestion point $PS_{ij'+1}$ on the reference line $\overline{B_iII_{ij+1}}$ obtained by the moving variance is the coordinate (236,193).

As listed in Table 5, the points 4, 5, and 6 show the largest angle, and the points with angles next to the largest angle are the points 1, 2, and 3 in order. Another reason why the angle value is an auxiliary index of features is that the coordinate (in the image) belongs discrete integer data. Generally, one point in a physical coordinate system has many surrounding azimuthal points (360° azimuthal angles) but one point in an integer coordinate system has only eight surrounding points (eight directions in a plane) in total. Hence, if the two reference segments are too close, the azimuthal angle is supposed to be limited by the influence of the distance, and thus the vector of the included angle subsequently output probably becomes acceptable.

TABLE 5

| k | 1 | 2 | 3 | 4 | 5 |
|---|---|---|---|---|---|
| $x_{AI_{ij+2k}}$ | 227 | 228 | 229 | 230 | 231 |
| $y_{AI_{ij+2k}}$ | 194 | 194 | 194 | 193 | 193 |
| $A_{ij+2k}$ | 0.994 | 0.992 | 0.990 | 1.000 | 1.000 |
| k | 6 | 7 | 8 | 9 | 10 |
| $x_{AI_{ij+2k}}$ | 232 | 233 | 234 | 235 | 236 |
| $y_{AI_{ij+2k}}$ | 193 | 192 | 192 | 192 | 192 |
| $A_{ij+2k}$ | 1.000 | 0.949 | 0.894 | 0.707 | 0.000 |
| k | 11 | 12 | 13 | 14 | 15 |
| $x_{AI_{ij+2k}}$ | 237 | 238 | 239 | 240 | 241 |
| $y_{AI_{ij+2k}}$ | 191 | 191 | 191 | 190 | 190 |
| $A_{ij+2k}$ | −0.447 | −0.707 | −0.832 | −0.800 | −0.857 |
| k | 16 | 17 | 18 | 19 | |
| $x_{AI_{ij+2k}}$ | 242 | 243 | 244 | 245 | |
| $y_{AI_{ij+2k}}$ | 190 | 189 | 189 | 189 | |
| $A_{ij+2k}$ | −0.894 | −0.868 | −0.894 | −0.914 | |

Figure 13:
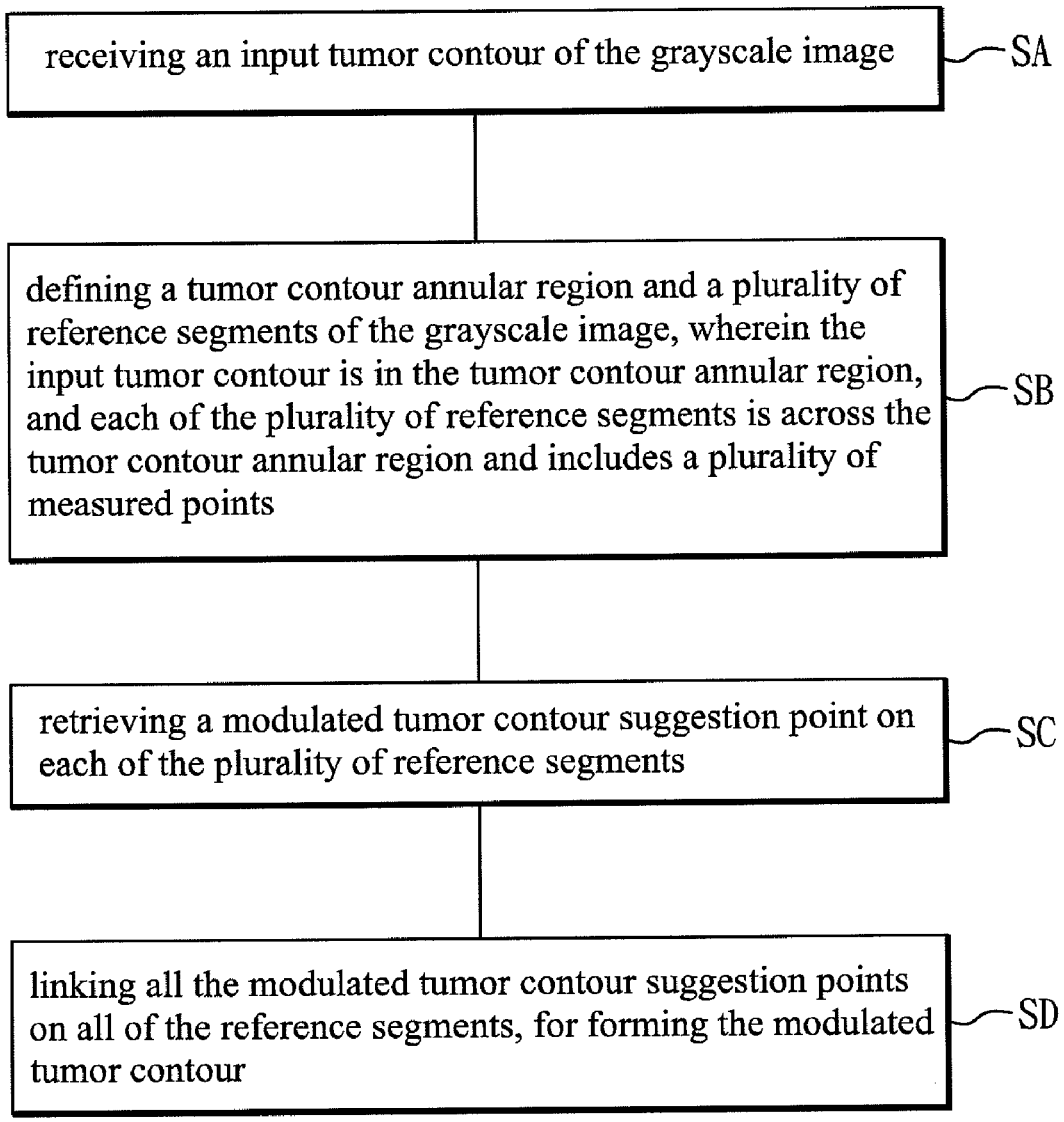
FIG. 13 is a flowchart of the method for retrieving a tumor contour of an image processing system according to the second embodiment of the present invention.

Please refer to FIG. 13, which is a flowchart of the method for retrieving a tumor contour of an image processing system according to the second embodiment of the present invention. The method for retrieving a tumor contour for an image processing system that includes a memory storing a grayscale image and a processor according to the second embodiment of the present invention comprises:

Step SA: receiving an input tumor contour of the grayscale image;

Step SB: defining a tumor contour annular region and a plurality of reference segments of the grayscale image, wherein the input tumor contour is in the tumor contour annular region, and each of the plurality of reference segments is across the tumor contour annular region and includes a plurality of measured points;

Step SC: retrieving a modulated tumor contour suggestion point on each of the plurality of reference segments; and Step SD: linking all the modulated tumor contour suggestion points on all of the reference segments, for forming the modulated tumor contour.

Besides, in step SC, the modulated tumor contour suggestion point on each of the plurality of reference segments is obtained by the following steps:

Step C1: normalizing the value of all the measured points on the reference segment retrieved by a moving variance retrieving method, the value of all the measured points on the reference segment retrieved by a contrast retrieving method, the value of all the measured points on the reference segment retrieved by a distance retrieving method, the value of all the measured points on the reference segment retrieved by a gradient EWMA difference retrieving method, and the value of all the measured points on the reference segment retrieved by an angle retrieving method into value between 0 and 1;

Step C2: determining modulating criteria for each of the aforementioned retrieving methods; calculating a weighting parameter for each the measured points on the reference segment, by multiplying product corresponding to each of the aforementioned retrieving methods together, wherein each of the products is obtained by multiple the normalized value of the measured point for the number of times equal to the modulating criteria of the corresponding retrieving method, respectively; and Step C3: retrieving the coordinate of the tumor contour suggestion point on the reference segment by calculating the average coordinate, from the sum of the product obtained by multiplying the coordinate of each of the measured points on the reference segment with the corresponding weighting parameter, respectively.

However, in the moving variance retrieving method applied in Step C1, each of the plurality of reference segments includes a plurality of local segments and each of the plurality of local segments includes a plurality of moving horizons; each of the plurality of local segments consists of one of the plurality of measured points, at least one measured point before and at least one measured point after the one of the plurality of measured points, and each of the plurality of moving horizons consists of one of the plurality of measured points in the corresponding local segment and at least one measured point after the one of the plurality of measured points; and the value of all the measured points on the reference segment are retrieved by the moving variance retrieving method comprising the steps of: calculating a gradient variance of the grayscale image in the plurality of local segments and an average gradient variance of the grayscale image in the plurality of moving horizons; calculating the ratio of the gradient variance of the grayscale image in the plurality of local segments to the average gradient variance of the grayscale image in the plurality of moving horizons; and retrieving the measured point corresponding to the maximum ratio as the tumor contour suggestion point.

On the other hand, in the contrast variance retrieving method applied in Step C1, a center of gravity of the input tumor contour is retrieved and a plurality of contrast reference segments is defined, each of the plurality of contrast reference segments extends from the center of the gravity to of the corresponding reference segments, respectively; and the value of all the measured points on the reference segment are retrieved by the contrast retrieving method comprising the steps of: calculating gradients of the grayscale image in the plurality of reference segments and an average gradient of the grayscale image in the plurality of contrast reference segments; calculating the differences between the gradients of the grayscale image in the plurality of reference segments and an average gradient of the grayscale image in the plurality of contrast reference segments; and retrieving the measured point corresponding to the maximum difference as the tumor contour suggestion point.

In the distance retrieving method applied in Step C1, the value of all the measured points on the reference segment are retrieved in sequence by the distance retrieving method comprising the steps of: when there are no tumor contour suggestion points before, taking one of the plurality of measured points on the first reference segment as a first point, or when there is one tumor contour suggestion point before, taking a last tumor contour suggestion point on one of the plurality of reference segments as the first point; taking one of the plurality of measured points on the next reference segment as a second point; and retrieving the measured point on the next reference segment, having the minimum distance between the first point and the second point as the tumor contour suggestion point on the next reference point.

In the gradient EWMA difference retrieving method applied in Step C1, the value of all the measured points on the reference segment are retrieved in sequence by the gradient EWMA difference retrieving method comprising the steps of: when there are no tumor contour suggestion points before, taking one of plurality of measured points on the first reference segment as a reference list; or when there is one tumor contour suggestion point before, taking all of the pervious tumor contour suggestion points as the reference list; providing an EWMA weighting formula; determining the weighting factor of the EWMA weighting formula and receiving the EWMA value of the reference list by the gradients of grayscale image of each of the measured points or the tumor contour suggestion points in the reference list; using the EWMA value of the reference list and the gradients of grayscale image of each of the plurality of measured points on the next reference segment as the input variables of the EWMA weighting formula; defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment.

At last, in the angle retrieving method applied in Step C1, the value of all the measured points on the reference segment are retrieved in sequence by the angle retrieving method comprising the steps of: when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point; defining a vector going from the first point to the second point as a first vector, and vectors going from the second point to each of the plurality of measured points on a next reference segment as a plurality of second vectors; calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

Since the above-mentioned 5 kinds of retrieving method have been described in Examples 1 to 5, the detailed explanation of these 5 kinds of retrieving method is omitted herein.

The abovementioned steps in the methods for retrieving a tumor contour of an image processing system of the present invention can be performed by computer programs. The software written for the methods for retrieving a tumor contour of an image processing system of the present invention can be stored in any recording media capable of being recognized or read by a microprocessing unit, or in any articles and devices including the recording medium. The articles are not limited, and can be hard discs, flexible discs, compact discs, ZIP, MO, IC chips, random-access memory (RAM), or any articles including the recording media known by one skilled in the art.

As the methods for retrieving a tumor contour of an image processing system is completely disclosed herein, one skill known the computer language can understand how to write software and computer programs. Accordingly, the detail referring to the software and computer programs related to the methods for retrieving a tumor contour of an image processing system of the present invention is not described herein.

Although the present invention has been explained in relation to its preferred embodiment, it is to be understood that many other possible modifications and variations can be made without departing from the scope of the invention as hereinafter claimed.

What is claimed is:

1. A method of retrieving a tumor contour implemented in an image processing system that includes a memory storing a grayscale image, a display screen, an input device and a processor performing method steps, comprising:
    receiving an input tumor contour of the grayscale image;
    defining a tumor contour annular region and a plurality of reference segments of the grayscale image, wherein the input tumor contour is in the tumor contour annular region, and each of the plurality of reference segments is across the tumor contour annular region and includes a plurality of measured points;
    retrieving a tumor contour suggestion point on each of the plurality of reference segments; and
    linking all the tumor contour suggestion points on all of the reference segments, for forming the tumor contour,
    wherein each of the plurality of reference segments includes a plurality of local segments and each of the plurality of local segments includes a plurality of moving horizons;
    wherein each of the plurality of local segments consists of one of the plurality of measured points, at least one measured point before and at least one measured point after the one of the plurality of measured points, and each of the plurality of moving horizons consists of one of the plurality of measured points in the corresponding local segment and at least one measured point after the one of the plurality of measured points; and
    wherein the tumor contour suggestion point is retrieved by a moving variance retrieving method comprising the steps of:
    calculating a gradient variance of the grayscale image in the plurality of local segments and an average gradient variance of the grayscale image in the plurality of moving horizons;
    calculating the ratio of the gradient variance of the grayscale image in the plurality of local segments to the average gradient variance of the grayscale image in the plurality of moving horizons; and
    retrieving the measured point corresponding to the maximum ratio as the tumor contour suggestion point.

2. A method of retrieving a tumor contour implemented in an image processing system that includes a memory storing a grayscale image, a display screen, an input device and a processor performing method steps, comprising:
    receiving an input tumor contour of the grayscale image;
    defining a tumor contour annular region and a plurality of reference segments of the grayscale image, wherein the input tumor contour is in the tumor contour annular region, and each of the plurality of reference segments is across the tumor contour annular region and includes a plurality of measured points;
    retrieving a modulated tumor contour suggestion point on each of the plurality of reference segments; and
    linking all the modulated tumor contour suggestion points on all of the reference segments, for forming the modulated tumor contour;
    wherein the modulated tumor contour suggestion point on each of the plurality of reference segments is obtained by the following steps:
    normalizing the value of all the measured points on the reference segment retrieved by a moving variance retrieving method, the value of all the measured points on the reference segment retrieved by a contrast retrieving method, the value of all the measured points on the reference segment retrieved by a distance retrieving method, the value of all the measured points on the reference segment retrieved by a gradient EWMA difference retrieving method, and the value of all the measured points on the reference segment retrieved by an angle retrieving method into value between 0 and 1;
    determining modulating criteria for each of the aforementioned retrieving methods;
    calculating a weighting parameter for each the measured points on the reference segment, by multiplying product corresponding to each of the aforementioned retrieving methods together, wherein each of the products is obtained by multiple the normalized value of the measured point for the number of times equal to the modulating criteria of the corresponding retrieving method, respectively; and
    retrieving the coordinate of the tumor contour suggestion point on the reference segment by calculating the average coordinate, from the sum of the product obtained by multiplying the coordinate of each of the measured points on the reference segment with the corresponding weighting parameter, respectively;
    wherein in the moving variance retrieving method, each of the plurality of reference segments includes a plurality of local segments and each of the plurality of local segments includes a plurality of moving horizons; each of the plurality of local segments consists of one of the plurality of measured points, at least one measured point before and at least one measured point after the one of the plurality of measured points, and each of the plurality of moving horizons consists of one of the plurality of measured points in the corresponding local segment and at least one measured point after the one of the plurality of measured points; and the value of all the measured points on the reference segment are retrieved by the moving variance retrieving method comprising the steps of:
    calculating a gradient variance of the grayscale image in the plurality of local segments and an average gradient variance of the grayscale image in the plurality of moving horizons;
    calculating the ratio of the gradient variance of the grayscale image in the plurality of local segments to the average gradient variance of the grayscale image in the plurality of moving horizons; and retrieving the measured point corresponding to the maximum ratio as the tumor contour suggestion point;

wherein in the contrast retrieving method, a center of gravity of the input tumor contour is retrieved and a plurality of contrast reference segments is defined, each of the plurality of contrast reference segments extends from the center of the gravity to of the corresponding reference segments, respectively; and the value of all the measured points on the reference segment are retrieved by the contrast retrieving method comprising the steps of:

calculating gradients of the grayscale image in the plurality of reference segments and an average gradient of the grayscale image in the plurality of contrast reference segments;

calculating the differences between the gradients of the grayscale image in the plurality of reference segments and an average gradient of the grayscale image in the plurality of contrast reference segments; and retrieving the measured point corresponding to the maximum difference as the tumor contour suggestion point;

wherein in the distance retrieving method, the value of all the measured points on the reference segment are retrieved in sequence by the distance retrieving method comprising the steps of:

when there are no tumor contour suggestion points before, taking one of the plurality of measured points on the first reference segment as a first point, or when there is one tumor contour suggestion point before, taking a last tumor contour suggestion point on one of the plurality of reference segments as the first point;

taking one of the plurality of measured points on the next reference segment as a second point; and retrieving the measured point on the next reference segment, having the minimum distance between the first point and the second point as the tumor contour suggestion point on the next reference point;

wherein in the gradient EWMA difference retrieving method, the value of all the measured points on the reference segment are retrieved in sequence by the gradient EWMA difference retrieving method comprising the steps of:

when there are no tumor contour suggestion points before, taking one of plurality of measured points on the first reference segment as a reference list; or when there is one tumor contour suggestion point before, taking all of the pervious tumor contour suggestion points as the reference list;

providing an EWMA weighting formula;

determining the weighting factor of the EWMA weighting formula and receiving the EWMA value of the reference list by the gradients of grayscale image of each of the measured points or the tumor contour suggestion points in the reference list;

using the EWMA value of the reference list and the gradients of grayscale image of each of the plurality of measured points on the next reference segment as the input variables of the EWMA weighting formula;

defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment;

wherein in the angle retrieving method, the value of all the measured points on the reference segment are retrieved in sequence by the angle retrieving method comprising the steps of:

when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point;

defining a vector going from the first point to the second point as a first vector, and vectors going from the second point to each of the plurality of measured points on a next reference segment as a plurality of second vectors;

calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

3. A method of retrieving a tumor contour implemented in an image processing system that includes a memory storing a grayscale image, a display screen, an input device and a processor performing method steps, comprising:

receiving an input tumor contour of the grayscale image;

defining a tumor contour annular region and a plurality of reference segments of the grayscale image, wherein the input tumor contour is in the tumor contour annular region, and each of the plurality of reference segments is across the tumor contour annular region and includes a plurality of measured points;

retrieving a tumor contour suggestion point on each of the plurality of reference segments; and linking all the tumor contour suggestion points on all of the reference segments, for forming the tumor contour, wherein a center of gravity of the input tumor contour is retrieved and a plurality of contrast reference segments is defined, each of the plurality of contrast reference segments extends from the center of the gravity to of the corresponding reference segments, respectively; and wherein the tumor contour suggestion point is retrieved by a contrast retrieving method comprising the steps of:

calculating gradients of the grayscale image in the plurality of reference segments and an average gradient of the grayscale image in the plurality of contrast reference segments;

calculating the differences between the gradients of the grayscale image in the plurality of reference segments and an average gradient of the grayscale image in the plurality of contrast reference segments; and retrieving the measured point corresponding to the maximum difference as the tumor contour suggestion point.

4. A method of retrieving a tumor contour implemented in an image processing system that includes a memory storing a grayscale image, a display screen, an input device and a processor performing method steps, comprising:

receiving an input tumor contour of the grayscale image;

defining a tumor contour annular region and a plurality of reference segments of the grayscale image, wherein the input tumor contour is in the tumor contour annular region, and each of the plurality of reference segments is across the tumor contour annular region and includes a plurality of measured points;

retrieving a tumor contour suggestion point on each of the plurality of reference segments; and linking all the tumor contour suggestion points on all of the reference segments, for forming the tumor contour, wherein the tumor contour suggestion point is retrieved in sequence by a distance retrieving method comprising the steps of:

when there are no tumor contour suggestion points before, taking one of the plurality of measured points on the first reference segment as a first point, or when there is one tumor contour suggestion point before, taking a last tumor contour suggestion point on one of the plurality of reference segments as the first point;

taking one of the plurality of measured points on the next reference segment as a second point; and retrieving the measured point on the next reference segment, having the minimum distance between the first point and the second point as the tumor contour suggestion point on the next reference point.

5. A method of retrieving a tumor contour implemented in an image processing system that includes a memory storing a grayscale image, a display screen, an input device and a processor performing method steps, comprising:

receiving an input tumor contour of the grayscale image;

defining a tumor contour annular region and a plurality of reference segments of the grayscale image, wherein the input tumor contour is in the tumor contour annular region, and each of the plurality of reference segments is across the tumor contour annular region and includes a plurality of measured points;

retrieving a tumor contour suggestion point on each of the plurality of reference segments; and linking all the tumor contour suggestion points on all of the reference segments, for forming the tumor contour, wherein the tumor contour suggestion point is retrieved in sequence by a gradient EWMA difference retrieving method comprising the steps of:

when there are no tumor contour suggestion points before, taking one of plurality of measured points on the first reference segment as a reference list; or when there is one tumor contour suggestion point before, taking all of the pervious tumor contour suggestion points as the reference list;

providing an EWMA weighting formula;

determining the weighting factor of the EWMA weighting formula and receiving the EWMA value of the reference list by the gradients of grayscale image of each of the measured points or the tumor contour suggestion points in the reference list;

using the EWMA value of the reference list and the gradients of grayscale image of each of the plurality of measured points on the next reference segment as the input variables of the EWMA weighting formula;

defining the output of the EWMA weighting formula as the EWMA value of each of the plurality of measured points on the next reference segment; and taking the one of plurality of measured points on the next reference segment, having the minimum difference between the gradient of grayscale image thereof and the EWMA value thereof, as the tumor contour suggestion point on the next reference segment.

6. A method of retrieving a tumor contour implemented in an image processing system that includes a memory storing a grayscale image, a display screen, an input device and a processor performing method steps, comprising:

receiving an input tumor contour of the grayscale image;

defining a tumor contour annular region and a plurality of reference segments of the grayscale image, wherein the input tumor contour is in the tumor contour annular region, and each of the plurality of reference segments is across the tumor contour annular region and includes a plurality of measured points;

retrieving a tumor contour suggestion point on each of the plurality of reference segments; and linking all the tumor contour suggestion points on all of the reference segments, for forming the tumor contour, wherein the tumor contour suggestion point is retrieved in sequence by an angle retrieving method comprising the steps of:

when there are no tumor contour suggestion point before a last tumor contour suggestion point, defining one of the plurality of measured points on the first reference segment as a first point, and one of the plurality of measured points on the second reference segment as a second point; or when there is one tumor contour suggestion point before the last tumor contour suggestion point, defining the tumor contour suggestion point before the last tumor contour suggestion point as the first point, and defining the last tumor contour suggestion point as the second point;

defining a vector going from the first point to the second point as a first vector, and vectors going from the second point to each of the plurality of measured points on a next reference segment as a plurality of second vectors;

calculating the cosine values of the angles included by the first vector and the plurality of second vectors, respectively; and taking the one of plurality of measured points on the second next reference segment, being the end point of the second vector corresponding to the angle having maximum cosine value, as the tumor contour suggestion point on the second next reference segment.

* * * * *